United States Patent [19]

Araki et al.

[11] Patent Number: 5,741,494
[45] Date of Patent: Apr. 21, 1998

[54] IMMUNOPOTENTIATIVE AND INFECTION-PROTECTIVE AGENT CONTAINING BACILLUS AND EGG WHITE

[75] Inventors: Seiichi Araki; Mamoru Suzuki; Masatoshi Fujimoto, all of Ibaraki, Japan

[73] Assignee: Eisai Co., Ltd., Japan

[21] Appl. No.: 530,385

[22] PCT Filed: Mar. 30, 1994

[86] PCT No.: PCT/JP94/00521

§ 371 Date: Oct. 31, 1995

§ 102(e) Date: Oct. 31, 1995

[87] PCT Pub. No.: WO94/22459

PCT Pub. Date: Oct. 13, 1994

[30] Foreign Application Priority Data

Apr. 7, 1993 [JP] Japan .................. 5-103701

[51] Int. Cl.⁶ .................. A61K 39/07; A61K 39/00; A61K 39/02; A61K 39/08
[52] U.S. Cl. .................. 424/246.1; 424/184.1; 424/234.1; 424/247.1; 426/32; 426/42; 426/43
[58] Field of Search .................. 424/246.1, 247.1, 424/234.1, 184.1; 426/32, 42, 43

[56] References Cited

U.S. PATENT DOCUMENTS 3,885,048  5/1975  Liggett .................. 426/18
4,107,334  8/1978  Jolly .................. 426/7

OTHER PUBLICATIONS

Derwent Abstract Accession No. 84–0020005 (Kimura 1974).

Derwent Abstract Accession No. 84–234713 (Tanaka 1984).

*Primary Examiner*—James C. Housel
*Assistant Examiner*—Jennifer Shaver
*Attorney, Agent, or Firm*—Nixno & Vanderhye

[57] ABSTRACT

Synergistic compositions of egg white and *Bacillus subtilis*, *Bacillus celleus*, *Lactobacillus lactis*, *Lactobacillus casei*, *Bifidobacterium bifidum* or Clostridium and optionally also containing garlic for treating and preventing infections and other uses are described.

7 Claims, 1 Drawing Sheet

IMMUNOPOTENTIATIVE AND INFECTION-PROTECTIVE AGENT CONTAINING BACILLUS AND EGG WHITE

FIELD OF THE INVENTION

The present invention relates to a medicine or food which potentiates an immune function of a human being or an animal to thereby protect the human being or the animal from infection, or a feed having an immunopotentiative action.

BACKGROUND OF THE INVENTION

In recent years, a progress in immunology has allowed to think that various maladies and infectious diseases of a human being and an animal are caused by the lowering or incompleteness in the immune function.

Various antibiotics have so far been administered for with such maladies or infectious diseases such as bronchial asthma, allergies and the like. Meanwhile, overcrowded raising conditions in the fields of animal husbandry and aquaculture in order to efficiently raise livestock, poultry or fish, dosing of antibiotics in a large amount has been employed. Such practices often give rise to the incidence of antibiotic-resistant bacillus.

Various materials having an immunopotentiative action has so far been investigated. It is known that *Bacillus subtilis Natto, Bacillus celleus, Bifidobacterium bifidum* and *Clostridium* have a little immunopotentiative action. With respect to egg white, the immunopotentiative action thereof has been reported by the present inventors (Japanese patent publication-A 3-251537).

SUMMARY OF THE INVENTION

Described are compositions safe for humans and animals comprising *Bacillus subtilis*, egg white and optionally also garlic can synergistically increase the respective immunopotentiative actions.

That is, the present invention relates to an immunopotentiative and infection-protective agent comprising two or more members in combination selected from bacillus, egg white and garlic. The above bacillus is selected from the group consisting of *Bacillus subtilis Natto, Bacillus celleus, Lactobacillus lactis, Lactobacillus casei, Bifidobacterium bifidum*, and *Clostridium*.

The invention relates to the use of the above defined combination of two or more members for the pharmacological treatment and prevention of human beings and animals. Accordingly the invention relates to a pharmacological composition and a feed composition.

The invention provides a pharmacological method for treating or preventing a disease by administering a pharmacologically effective amount of the combination to human being or an animal by virtue of an immunopotentiative action, an infection protective action and/or an infection preventing action to provide by the combination of the invention.

Bacillus may, in the invention, include *Bacillus substilis Natto, Streptococcus faecalis, Clostridium butyricum, Lactobacillus lactis* and *Bifidobacterium bifidum*.

Bacillus may further includes Bacillaceae, Enterococcus and Lactobacillaceae. It may further includes Bacillus, Streptococcus, Clostridium and Lactobacillus.

Egg white includes natural egg white powder, egg white powder produced by fermenting with a bacillus or an enzyme to remove saccharides, sterilizing and drying and egg white powder produced by fermenting with a digesting enzyme.

The bacillus used in the present invention is selected from the bacilli described above. The condition of the bacillus is not specifically limited, and either raw bacillus or dead bacillus can be used. They are commercially available and can readily be obtained. A nutrient type is preferred.

The egg white used in the present invention is not specifically limited, and there can be used raw egg white, whole egg powder, or enzyme-treated egg white, and those containing a component constituting the egg white.

The processes of preparing the egg white will be shown below.

(1) Raw egg white is subjected to a fermentation treatment (desugar treatment) with bacteria or fungus (e.g., yeast) and a sterilization treatment and then to drying and a pulverization treatment to prepare egg white powder.

(2) Raw egg white is subjected to a fermentation treatment (desugar treatment) with bacteria or fungus (e.g., yeast) and a sterilization treatment. The egg white thus treated is subjected to removal of lysozyme with a conventional ion exchange resin deposition process or isoelectric crystallization process and then to drying to prepare egg white powder.

(3) Raw egg white is subjected to an enzyme (digestive enzyme and others) treatment.

(4) Raw egg white is subjected to a fermentation treatment (desugar treatment) with bacteria or fungus (e.g., yeast) and a sterilization treatment and then to an enzyme (digestive enzyme and others) treatment.

Further, garlic bulbs are used in the present invention, and the form is not specifically limited. The form may be raw or dried, as long as a component constituting the garlic bulb is present.

The term "immunopotentiation" used in the present invention means the potentiation of an immune function of a human being, livestock, poultry, fish, or an animal including pets.

Accordingly, the increase in the immune function of a human being or an animal by the present invention allows the present invention to be useful for the prevention and treatment of various diseases and as a preventive and therapeutic agent for various infectious diseases.

Further, the infectious disease of a cultivated fish or fish to which the present invention is applied is not specifically limited, and it is extended over a wide range of, for example, bacterial diseases such as streptococcosis and nodosity, and viral infectious diseases.

The dosage of the immunopotentiative and infection-protective agent in the present invention is not specifically limited since it is varied according to a dosing form and an animal to which it is dosed.

For example, administering it to a livestock such as a pig, the dosage is usually 5 mg or more, preferably 10 mg or more, and further preferably 50 mg or more per kg of the body weight. Using it for a feed, the dosage is adjusted in an ordinary manner so that it becomes the same dosage as that described above. Dosing to a human being, the dosage therefor also corresponds thereto.

The present invention comprises two or more members in combination selected from bacillus, egg white and garlic. The compounding ratio of the two members is not specifically limited, and it is usually 1:1 to 100, preferably 1:1 to 50, further preferably 1:20 in terms of a weight ratio. Among them, a preferred combination is bacillus and egg white or garlic and egg white.

Further, the compounding ratio of bacillus, egg white and garlic is not specifically limited. Usually, it is 1:1 to 100:1 to 100, preferably 1:1 to 50:1 to 50, and further preferably 1:1 to 20:1 to 20.

The dosing form of the immunopotentiative and infection-protective agent according to the present invention is not specifically limited. In the case where it is administered to a livestock and a poultry, it can be dosed, mixed with a feed.

Accordingly, the present invention provides a feed comprising two or more members in combination selected from bacillus, egg white and garlic and having an immunopotentiative and infection-protective action, wherein the above bacillus is one or more members selected from the group consisting of *Bacillus subtilis Natto*, *Bacillus celleus*, *Lactobacillus lactis*, *Bifidobacterium bifidum*, and Clostridium.

Further, the immunopotentiative and infection-protective agent according to the present invention can be added to a food to use as a food which is specifically aimed at the protection of the respective diseases and has a biological controlling function, i.e., a so-called functional food.

Further, the immunopotentiative and infection-protective agent according to the present invention does not have a problem on an influence by a resistant bacillus and residue, which is the case with an antibiotic, and therefore it can be used as well for a livestock such as pig, chicken, cow, and sheep, fish, and a pet (a dog, a cat and a bird) as a safe feed having a biological protective and controlling function, i.e., a functional feed.

In the case where the present invention is administered as a medicine or a so-called health food, it can be formulated into tablet, granule, powder, capsule or syrup. These preparations can be manufactured by mixing those comprising two or more members in combination selected from bacillus, egg white and garlic with a conventional filler, binder and lubricant for a pharmaceutical use by a conventional process.

It can be found from the following tests that the immunopotentiative and infection-protective agent according to the present invention has an excellent infection-protective action.

[EXAMPLE]

Figure 1:
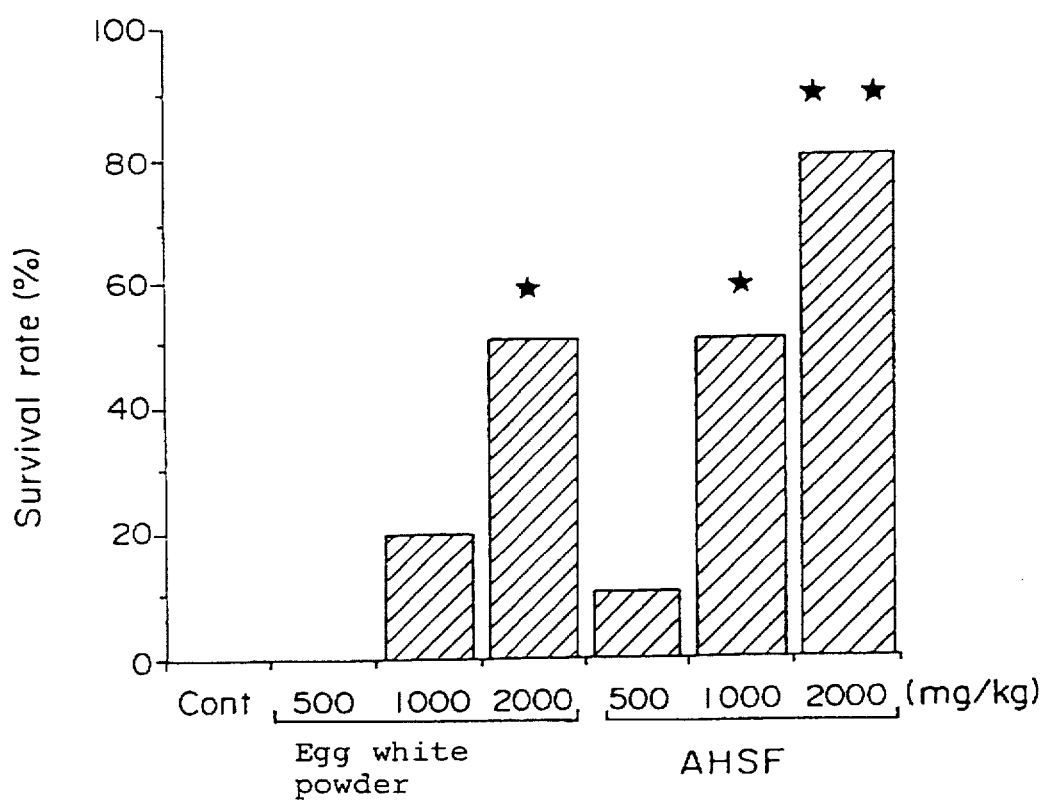
FIG. 1 shows the results of the experiment described in Example 11.

The present invention will concretely be explained below by reference to the examples. The description on the dosage of the substances used in the examples, for example, "10 mg/kg p.o." means oral administration of 10 mg per kg of a body weight. Further, the symbols "*" and "**" used in the column of a $x^2$ test in Tables 1 to 3 mean $p<0.05$ and $p<0.01$, respectively.

Example 1

*Bacillus subtilis Natto*, egg white and garlic were orally administered to ten SLC:ICR male mice (age: 5 to 6 weeks, body weight: 26 to 33 g) in the combinations and amounts shown in Table 1, while physiological saline was orally administered thereto as a control. After 24 hours, clinically available *Escherichia coli* ($5.0 \times 10^7$ CFU/mouse, 0.2 ml) was intravenously inoculated into each mouse to obtain a survival rate based on the number of mice surviving after 7 days from the infection. The results are shown in Table 1.

*Bacillus subtilis Natto* was used in the form of bacillus which was killed by freezing and melting. Egg white powder was obtained by subjecting raw egg white to a fermantation (desugar treatment) and a sterilizing treatment and then to drying.

TABLE 1

| Sample | Survival rate | $x^2$ test |
|---|---|---|
| Control (physiological saline p.o.) | 0 | |
| *Bacillus subtilis* Natto $1.0 \times 10^8$ (bacillus amount: CFU/mouse p.o.) | 20 | |
| Garlic powder 500 mg/kg p.o. | 10 | |
| Egg white powder 2000 mg/kg p.o. | 50 | * |
| Egg white powder 2000 mg/kg p.o. Garlic powder 500 mg/kg p.o. | 90 | ** |
| Egg white powder 2000 mg/kg p.o. *Bacillus subtilis* Natto $1.0 \times 10^8$ (bacillus amount: CFU/mouse p.o.) | 90 | ** |
| Egg white powder 2000 mg/kg p.o. *Bacillus subtilis* Natto $1.0 \times 10^8$ CFU/mouse p.o. Garlic powder 500 mg/kg p.o. | 100 | ** |

Example 2

An experiment was carried out in the same manner as that in Example 1 except that *Bacillus subtilis Natto* and garlic were orally administered to a mouse in the combinations and amounts shown in Table 2. The results are shown in Table 2.

TABLE 2

| Sample | Survival rate (%) | $x^2$ test |
|---|---|---|
| Control | 0 | |
| N 500 mg/kg | 20 | |
| N 1 g/kg | 40 | * |
| N 2 g/kg | 70 | ** |
| BN $10^7$ CFU/mouse | 10 | |
| BN $10^8$ CFU/mouse | 40 | * |
| BN $10^9$ CFU/mouse | 80 | ** |
| N 500 mg/kg + BN $10^9$ CFU/mouse | 100 | ** |
| N 1 g/kg + BN $10^8$ CFU/mouse | 100 | ** |
| N 2 g/kg + BN $10^7$ CFU/mouse | 100 | ** |

N; garlic, BN: *Bacillus subtilis* Natto

Example 3

An experiment was carried out in the same manner as that in Example 1 except that *Streptococcus faecalis* and garlic were orally administered to a mouse in the combinations and amounts shown in Table 3. The results are shown in Table 3.

TABLE 3

| Sample | Survival rate (%) | $x^2$ test |
|---|---|---|
| Control | 0 | |
| N 500 mg/kg | 20 | |
| N 1 g/kg | 40 | * |
| N 2 g/kg | 70 | ** |
| SF $10^7$ CFU/mouse | 0 | |
| SF $10^8$ CFU/mouse | 20 | |
| SF $10^9$ CFU/mouse | 40 | * |
| N 500 mg/kg + SF $10^9$ CFU/mouse | 70 | ** |
| N 1 g/kg + SF $10^8$ CFU/mouse | 70 | ** |
| N 2 g/kg + SF $10^7$ CFU/mouse | 80 | ** |

SF: *Streptococcus faecalis*

Example 4

An experiment was carried out in the same manner as that in Example 1 except that *Streptococcus faecalis* and egg white were orally administered to a mouse in the combinations and amounts shown in Table 4. The results are shown in Table 4.

TABLE 4

| Sample | Survival rate (%) | $x^2$ test |
|---|---|---|
| Control | 0 | |
| EW 500 mg/kg | 10 | |
| EW 1 g/kg | 30 | |
| EW 2 g/kg | 50 | * |
| SF $10^7$ CFU/mouse | 0 | |
| SF $10^8$ CFU/mouse | 20 | |
| SF $10^9$ CFU/mouse | 40 | * |
| EW 2 g/kg + SF $10^7$ CFU/mouse | 60 | ** |
| EW 1 g/kg + SF $10^8$ CFU/mouse | 90 | ** |
| EW 2 g/kg + SF $10^9$ CFU/mouse | 100 | ** |

Example 5

An experiment was carried out in the same manner as that in Example 1 except that *Bifidobacterium bifidum*, egg white and garlic were orally administered to a mouse in the combinations and amounts shown in Table 5. The results are shown in Table 5.

TABLE 5

| Sample | Survival rate (%) | $x^2$ test |
|---|---|---|
| Control | 0 | |
| EW 500 mg/kg | 10 | |
| EW 1 g/kg | 30 | |
| EW 2 g/kg | 50 | * |
| N 500 mg/kg | 20 | |
| N 1 g/kg | 40 | * |
| N 2 g/kg | 70 | ** |
| BB $10^7$ CFU/mouse | 0 | |
| BB $10^8$ CFU/mouse | 30 | |
| BB $10^2$ CFU/mouse | 50 | * |
| EW 500 mg/kg + N 500 mg/kg + BB $10^9$ CFU/mouse | 90 | ** |
| EW 1 g/kg + N 1 g/kg + BB $10^8$ CFU/mouse | 100 | ** |

BB: *Bifidobacterium bifidum*

Example 6

An experiment was carried out in the same manner as that in Example 1 except that Clostridium and garlic were orally administered to a mouse in the combinations and amounts shown in Table 6. The results are shown in Table 6.

TABLE 6

| Sample | Survival rate (%) | $x^2$ test |
|---|---|---|
| Control | 0 | |
| N 500 mg/kg | 20 | |
| N 1 g/kg | 40 | * |
| N 2 g/kg | 70 | ** |
| CB $10^7$ CFU/mouse | 10 | |
| CB $10^8$ CFU/mouse | 30 | ** |
| CB $10^9$ CFU/mouse | 60 | ** |
| N 500 mg/kg + CB $10^9$ CFU/mouse | 90 | ** |
| N 1 g/kg + CB $10^8$ CFU/mouse | 90 | ** |
| N 2 g/kg + CB $10^7$ CFU/mouse | 100 | ** |

CB: *Clostridium butyricam*

Example 7

An experiment was carried out in the same manner as that in Example 1 except that *Bacillus subtilis Natto*, egg white and garlic were orally administered to a mouse in the combinations and amounts shown in Table 7. The results are shown in Table 7.

TABLE 7

| Sample | Survival rate (%) | $x^2$ test |
|---|---|---|
| Control | 0 | |
| EW 500 mg/kg | 10 | |
| EW 1 g/kg | 30 | |
| EW 2 g/kg | 50 | * |
| N 500 mg/kgf | 20 | |
| N 1 g/kg | 40 | * |
| N 2 g/kg | 70 | ** |
| BN $10^7$ CFU/mouse | 10 | |
| BN $10^8$ CFU/mouse | 40 | |
| BN $10^9$ CFU/mouse | 80 | * |
| EW 500 mg/kg + BN $10^7$ CFU/mouse | 30 | |
| EW 500 mg/kg + BN $10^8$ CFU/mouse | 80 | ** |
| EW 500 mg/kg + BN $10^2$ CFU/mouse | 100 | ** |
| EW 500 mg/kg + N 500 mg/kg + BN $10^8$ CFU/mouse | 100 | ** |
| EW 1 g/kg + N 1 g/kg + BN $10^7$ CFU/mouse | 100 | ** |

Example 8

An experiment was carried out in the same manner as that in Example 1 except that *Streptococcus faecalis*, egg white and garlic were orally administered to a mouse in the combinations and amounts shown in Table 8. The results are shown in Table 8.

TABLE 8

| Sample | Survival rate (%) | $x^2$ test |
|---|---|---|
| Control | 0 | |
| EW 500 mg/kg | 10 | |
| EW 1 g/kg | 30 | |
| EW 2 g/kg | 50 | * |
| N 500 mg/kg | 20 | |
| N 1 g/kg | 40 | * |
| N 2 g/kg | 70 | ** |
| SF $10^7$ CFU/mouse | 0 | |
| SF $10^8$ CFU/mouse | 20 | |
| SF $10^9$ CFU/mouse | 40 | * |
| EW 500 mg/kg + N 500 mg/kg + SF $10^9$ CFU/mouse | 80 | ** |
| EW 1 g/kg + N 1 g/kg + SF $10^8$ CFU/mouse | 100 | ** |

Example 9

An experiment was carried out in the same manner as that in Example 1 except that *Bifidobacterium bifidum*, egg white and garlic were orally administered to a mouse in the combinations and amounts shown in Table 9. The results are shown in Table 9.

TABLE 9

| Sample | Survival rate (%) | $x^2$ test |
|---|---|---|
| Control | 0 | |
| N 500 mg/kg | 20 | |
| N 1 g/kg | 40 | * |
| N 2 g/kg | 70 | ** |
| EW 500 mg/kg | 10 | |
| EW 1 g/kg | 30 | |
| EW 2 g/kg | 50 | * |
| BB $10^7$ CFU/mouse | 0 | |
| BB $10^8$ CFU/mouse | 30 | |
| BB $10^9$ CFU/mouse | 50 | * |
| EW 500 mg/kg + BB $10^9$ CFU/mouse | 80 | ** |
| EW 1 g/kg + BB $10^8$ CFU/mouse | 80 | ** |
| EW 2 g/kg + BB $10^7$ CFU/mouse | 90 | ** |
| EW 2 g/kg + BB $10^7$ CFU/mouse | 50 | * |
| EW 2 g/kg + BB $10^8$ CFU/mouse | 80 | ** |
| EW 2 g/kg + BB $10^9$ CFU/mouse | 100 | ** |

Example 10

An experiment was carried out in the same manner as that in Example 1 except that Clostridium, egg white and garlic were orally administered to a mouse in the combinations and amounts shown in Table 10. The results are shown in Table 10.

TABLE 10

| Sample | Survival rate (%) | $x^2$ test |
|---|---|---|
| Control | 0 | |
| EW 500 mg/kg | 10 | |
| EW 1 g/kg | 30 | |
| EW 2 g/kg | 50 | * |
| N 500 mg/kg | 20 | |
| N 1 g/kg | 40 | * |
| N 2 g/kg | 70 | ** |
| CB $10^7$ CFU/mouse | 10 | |
| CB $10^8$ CFU/mouse | 30 | |
| CB $10^9$ CFU/mouse | 60 | ** |
| EW 500 mg/kg + CB $10^9$ CFU/mouse | 60 | ** |
| EW 1 g/kg + CB $10^8$ CFU/mouse | 90 | ** |
| EW 2 g/kg + CB $10^7$ CFU/mouse | 100 | ** |
| EW 500 mg/kg + N 500 mg/kg + CB $10^9$ CFU/mouse | 100 | ** |
| EW 1 g/kg + N 1 g/kg + CB $10^8$ CFU/mouse | 100 | ** |

Example 11

An experiment was carried out in the same manner as that in Example 1 except for using a preparation of egg white powder or a composition (abbreviated as AHSF) obtained by mixing Bacillus subtilis Natto at $10^9$ CFU, starch as a filler, egg white powder and garlic in the weight ratio of 1:1:1 were orally administered to a mouse in the amounts shown in FIG. 1. The results are shown in FIG. 1.

As shown in Tables 1 to 10 and FIG. 1, the immunopotentiative and infection-protective agent according to the present invention showed higher effects against (synergistic effect) Escherichia coli infection than the sum (additive effect) of each single infection-protective effect.

The preparation of egg white powder and the AHSF each were orally administered to ten SLC:ICR male mice (age: 5 to 6 weeks, body weight: 26 to 33 g) in the amounts shown in Table 11 for 5 days (once per day) before inoculating virus, immediately after inoculating virus, one day after inoculating virus, and two days after inoculating virus (totally eight times). Sterilized water 0.5 ml was orally administered to a mouse for control.

Clinically available Aujesky virus 6.25 PFU/mouse was intraperitoneally inoculated into each mouse to obtain a survival rate based on the number of mice surviving on the seventh day after an infection. Results are shown in Table 11.

TABLE 11

| Sample | Survival rate (%) | $x^2$ test |
|---|---|---|
| Control 0.5 ml | 20 | |
| Egg white powder 500 mg/kg | 20 | |
| Egg white powder 1 g/kg | 50 | * |
| Egg white powder 2 g/kg | 50 | * |
| AHSF 500 mg/kg | 30 | |
| AHSF 1 g/kg | 60 | ** |
| AHSF 2 g/kg | 70 | ** |

It has been oberved that AHSF reveals an immunoprotective effect against Aujesky virus infection by oral administration. In a pig, the dosage of AHSF can be reduced and therefore it can be expected that AHSF according to the present invention will be useful to a pig Aujesky disease.

What is claimed is:

1. A method of treating an *Escherichia coli* infection comprising orally administering to an animal a therapeutically effective amount of a synergistic combination of egg white, garlic and at least one microorganism selected from the group consisting of *Bacillus subtilis*, *Bacillus celleus*, *Lactobacillus lactis*, *Lactobacillus casei*, *Bifidobacterium bifidum* and Clostridium.

2. A method of treating an *Escherichia coli* infection comprising orally administering to an animal a therapeutically effective amount of a synergistic combination of garlic and at least one microorganism selected from the group consisting of *Bacillus subtilis*, *Bacillus celleus*, *Lactobacillus lactis*, *Lactobacillus casei*, *Bifidobacterium bifidum* and Clostridium.

3. A method of treating an *Escherichia coli* infection comprising orally administering to an animal a therapeutically effective amount of a synergistic combination of egg white and at least one microorganism selected from the group consisting of *Bacillus subtilis*, *Bacillus celleus*, *Lactobacillus lactis*, *Lactobacillus casei*, *Bifidobacterium bifidum* and Clostridium.

4. The method as claimed in claim 2 wherein the bacteria is *Bacillus subtilis* and the subspecies is *Bacillus subtilis* Natto.

5. The method as claimed in claim 3 wherein the combination consists essentially of *Bacillus subtilis* Natto and egg white.

6. The method as claimed in claim 1 wherein the combination consists essentially of *Bacillus subtilis* Natto, egg white and garlic.

7. A method of treating an *Escherichia coli* infection comprising orally administering to an animal in need of same a therapeutically effective amount of a synergistic combination of egg white and garlic.

* * * * *